United States Patent [19]
Markowitz

[11] Patent Number: 5,233,983
[45] Date of Patent: Aug. 10, 1993

[54] METHOD AND APPARATUS FOR APNEA PATIENT SCREENING

[75] Inventor: H. Toby Markowitz, Roseville, Minn.

[73] Assignee: Medtronic, Inc., Minneapolis, Minn.

[21] Appl. No.: 754,407

[22] Filed: Sep. 3, 1991

[51] Int. Cl.$^5$ ............................................. A61N 1/36
[52] U.S. Cl. ..................................... 607/42; 128/671
[58] Field of Search .......... 128/419 G, 419 R, 419 C, 128/420 A, 420 R, 421, 422, 786, 721, 905, 716, 720, 670, 671

[56] References Cited

U.S. PATENT DOCUMENTS

| | | | |
|---|---|---|---|
| 4,506,666 | 3/1985 | Durkan | 128/204.23 |
| 4,827,935 | 5/1989 | Geddes et al. | 128/419 G |
| 4,830,008 | 5/1989 | Meer | 128/421 |
| 4,945,899 | 8/1990 | Sugiyama et al. | 128/721 |
| 4,982,738 | 1/1991 | Griebel | 128/716 |
| 5,056,519 | 10/1991 | Vince | 128/419 G |
| 5,111,814 | 5/1992 | Goldfarb | 128/419 R |

OTHER PUBLICATIONS

"Obstructive Sleep Apnea: Diagnosis and Treatment", William R. Cook, M.D. and J. David Osguthorpe, M.D., *JSC Medical Association*, vol. 81(12), Dec. 1985, pp. 647–651.

"Effects of Submental Electrical Stimulation During Sleep on Upper Airway Patency in Patients with Obstructive Sleep Apnea" by Hiroshi Miki et al., *American Review of Respiratory Disease*, 1989 vol. 140, pp. 1285–1289.

"Motor Prostheses", by J. T. Mortimer, *Handbook of Physiology, Section 1: The Nervous System*, vol. II Motor Control, part 1, pp. 178–179.

"Diaphragm Pacing: Present Status", by William W. L. Glenn, *PACE*, vol. 1, Jul.–Sep. 1978, pp. 357–370.

*Primary Examiner*—Kyle L. Howell
*Assistant Examiner*—George Manuel
*Attorney, Agent, or Firm*—John L. Rooney

[57] ABSTRACT

An apparatus for and method of preoperative and intraoperative screening of obstructive sleep apnea patients. The screening device employs a plurality of stimulation channels which may be individually controlled to terminate or prevent an apnea event. The apparatus also contains a plurality of sensor processing channels to permit selection of the optimal sensor configuration and the sensing parameters. The preoperative procedure determines the suitability of a patient for therapy using an automatic implantable system. The type and placement of sensors and stimulation electrodes is also determined. During the intraoperative procedure, the initial screening determinations are verified and the various sensing and stimulation parameters are optimized.

11 Claims, 8 Drawing Sheets

METHOD AND APPARATUS FOR APNEA PATIENT SCREENING

CROSS REFERENCE TO CO-PENDING APPLICATIONS

U.S. patent application Ser. No. 07/610,854, filed Nov. 8, 1990, entitled Muscle Tone; U.S. patent application Ser. No. 07/639,192, filed Jan. 9, 1991, entitled Servo Muscle Control; U.S. patent application Ser. No. 07/617,158, filed Nov. 23, 1990, entitled Multiple Stimulation Electrodes; U.S. patent application Ser. No. 07/671,513, filed Mar. 19, 1991, now U.S. Pat. No. 5,146,918, issued Sep. 15, 1992, entitled Demand Apnea Control; U.S patent application Ser. No. 07/679,120, filed Apr. 2, 1991, entitled Apnea Treatment System with Ramp On Generator; U.S. patent application Ser. No. 07/706,165, filed May 20, 1991, entitled Apnea System with Airway Feedback Monitoring; and U.S. patent application Ser. No. 07/719,929, , filed Jun. 24, 1991, entitled Apnea Stimulation Lead; are all assigned to the assignee of the present invention and incorporated herein by reference.

BACKGROUND OF THE INVENTION

1. Field of the Invention

The present invention relates generally to medical devices and methods and more particularly relates to techniques for the treatment of obstructive sleep apnea.

2. Description of the Prior Art

The medical characteristics of sleep apnea have been known for some time. There are two generally recognized forms of the disease. The first is central sleep apnea which is associated with the failure of the body to automatically generate the neuro-muscular stimulation necessary to initiate and control a respiratory cycle at the proper time. Work associated with employing electrical stimulation to treat this condition is discussed in "Diaphragm Pacing: Present Status", by William L. Glenn, in *Pace*, Volume I, at pages 357-370 (July-September 1978). The second condition is known as obstructive sleep apnea. It is discussed at some length in "Obstructive Sleep Apnea: Diagnosis and Treatment", by Drs. Cook and Osguthorpe in *Journal of South Carolina Medical Association*, 81 (12): 647-651 (December 1985).

At present, a tracheostomy may be the treatment of choice for a number of patients when obstructive sleep apnea is severe, although systems employing continuous positive air pressure (CPAP) are now available. However, some interest has been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator.

The use of an implantable system for the treatment of obstructive sleep apnea by stimulation of the muscles of the upper airway is not indicated for all patients. Furthermore, for those patients for whom this therapy is indicated, placement of electrodes and sensors and adjustment of certain basic sensing and stimulation parameters is required. At present, the prior art does not teach an efficient method to accomplish the necessary screening of patients nor appropriate apparatus to assist in component placement and parameter adjustment.

SUMMARY OF THE INVENTION

The present invention overcomes the disadvantages of the prior art by providing a methodology for performing preoperative and intraoperative screening of obstructive sleep apnea patients. The preoperative screening provides an opportunity to select which patients are indicated for therapy using an implantable muscle stimulation system. Intraoperative screening enables efficient placement of the various components and selection of the most suitable sensing and stimulation parameters. The present invention also provides a hardware system to effectively perform preoperative and intraoperative screening.

The first step in the preoperative technique is to determine if a particular patient experiences identifiable episodes of obstructive sleep apnea. This may be accomplished using techniques and methods which are well established in the medical literature. If the patient is so identified, the effectiveness of various electrodes types and locations are tested. Electrical muscle stimulation may be contraindicated if a practical electrode type and location can not be determined. Various sensor types are tested to determine the type and location providing the most effective detection combination.

The intraoperative procedure is similar except that electrode and sensor types have been preselected. However, even though gross locations have been determined, optimal positions are more accurately chosen intraoperatively. Sensor and stimulation parameters are found precisely before the surgery is completed.

The present invention also provides an apparatus to effectively perform these procedures. EKG and respiratory EMG signals may be used as physiological controls when viewing the timing of the sensing and stimulation signals.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4, comprising

FIG. 5, comprising

DETAILED DESCRIPTION OF THE PREFERRED EMBODIMENTS

Figure 1:
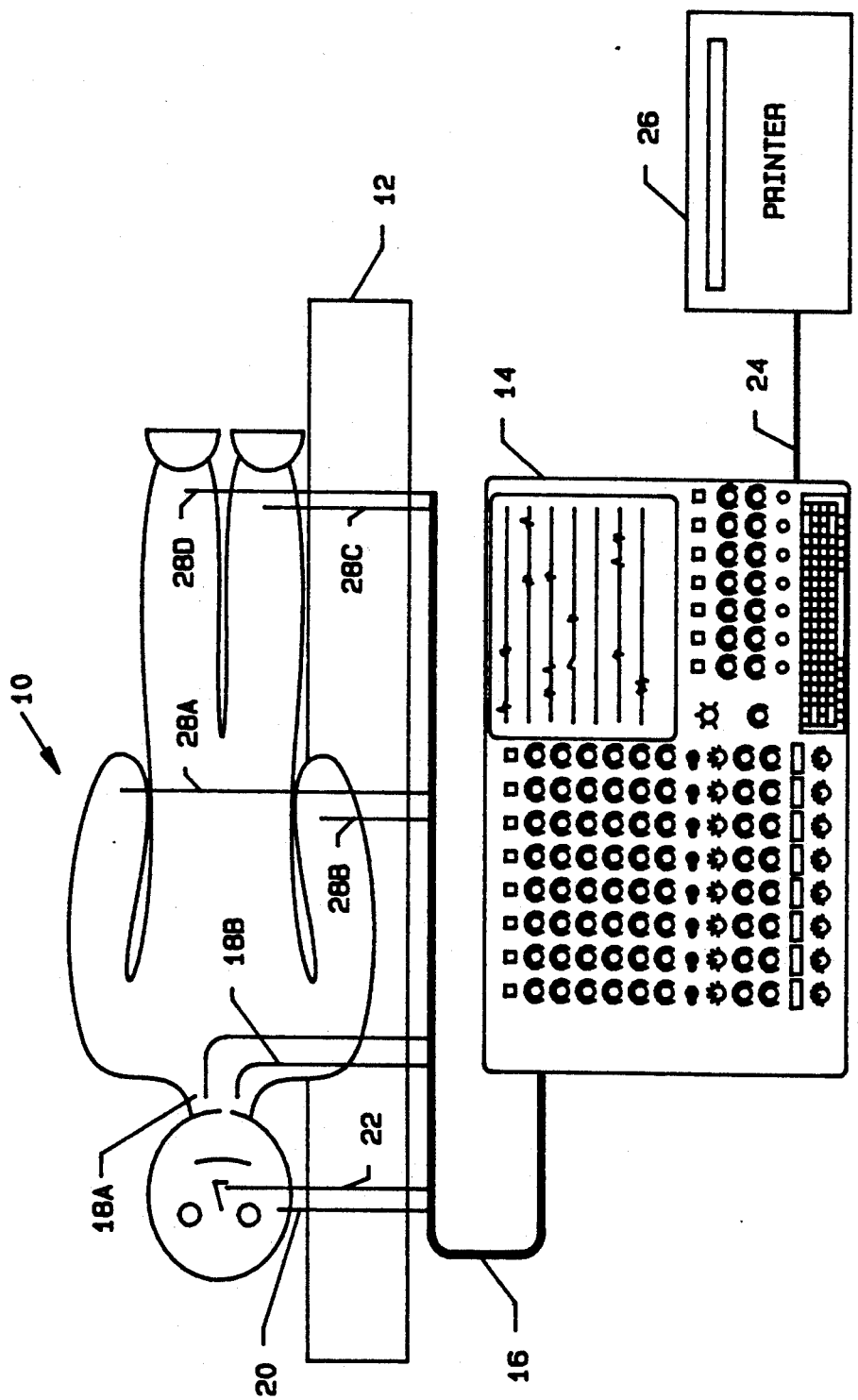
FIG. 1 is a schematic view of a patient undergoing a screening procedure.

FIG. 1 is a schematic view of patient 10 undergoing a typical screening procedure. Patient 10 is reclining on standard examination table 12. Cable 16 couples various electrodes and sensors placed on patient 10 to screening device 14. Printer 26 is coupled to screening device 14 via cable 24. Printer 26 is used to make an optional hardcopy record of the screening procedure.

Cable 16 couples the screening device 14 to patient 10. Of the various connections made thereby is the lead 20 which may be used for coupling to a standard ear densitometer, audio sensor, and other external sensing devices. Similarly, cable 22 couples to the sensors within the airway including pressure, differential pressure, audio, airflow, and muscle strain. Cables 28A, 28B, 28C, and 28D are coupled to the limbs of patient 10 to provide the most common EKG lead configurations.

Cables 18A and 18B representatively couple to the various possible electrode placement positions.

Figure 2:
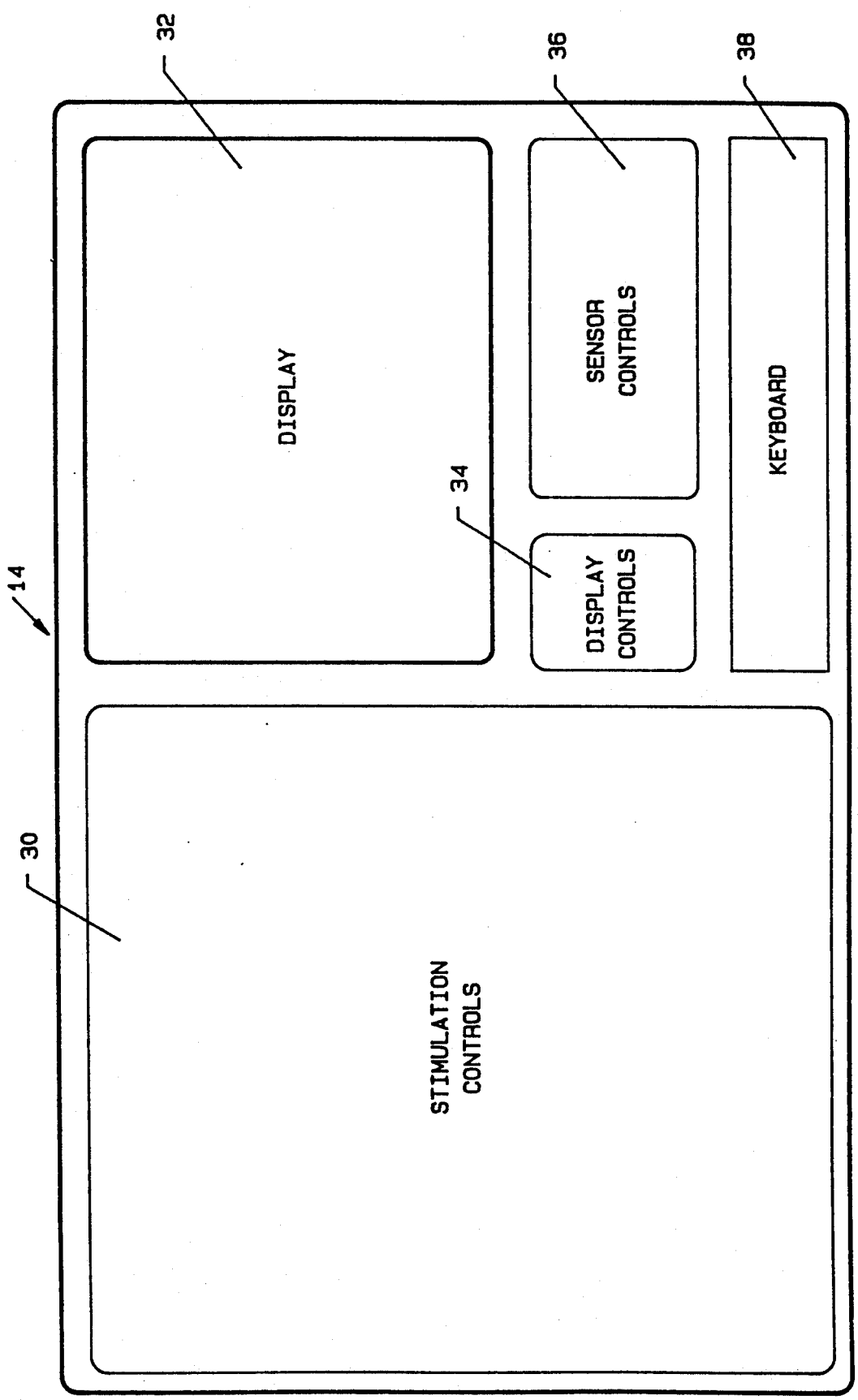
FIG. 2 shows the basic layout of the front panel of the screening device.

FIG. 2 is a plan view of the front panel of screening device 14. The detail has been abbreviated to permit the viewer to observe the major portions of the operator controls and monitors. Area 30 contains the stimulation controls. It is in area 30 that all of the controls to vary stimulation parameters and timing are located. CRT display 32 is used to view outputs of sensors to permit selection and synchronization of the various sensor types.

Area 34 contains the controls for the CRT display. These controls provide for synchronization of the signals displayed to certain standards for visual analysis. Area 36 contains all of the controls which regulate the sensors deployed on patient 10. Keyboard 38 permits the operator to make various alpha-numeric entries to annotate and comment upon the data which is displayed and recorded. A convenient data storage medium (not shown), such as a floppy disk drive may be added to more completely save the test results.

Figure 3:
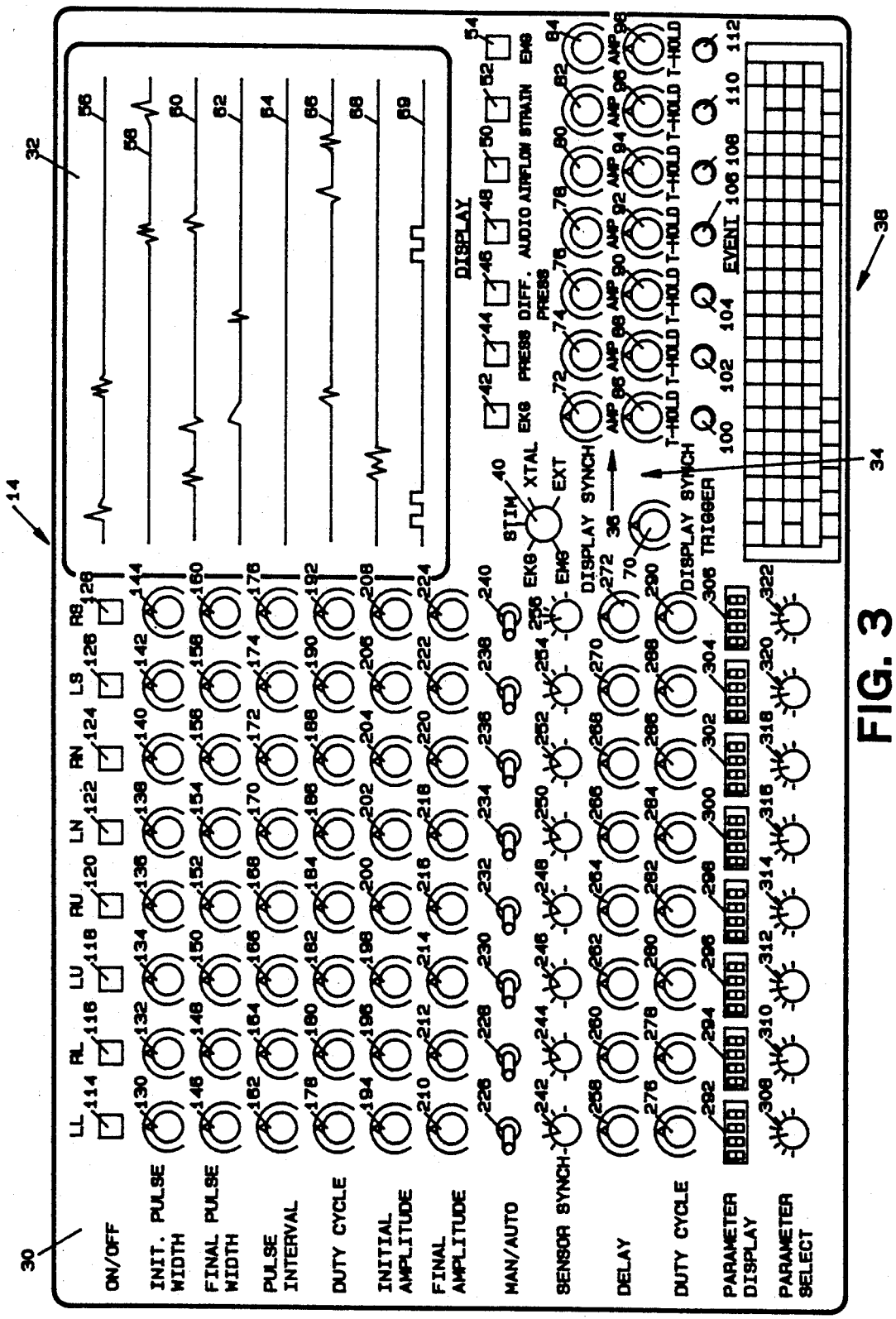
FIG. 3 is a detailed view of the front panel of the screening device.

FIG. 3 provides a detailed view of all of the operator actuated controls of the front panel of screening device 14. Multiposition control 40 selects the timing signal for synchronization of CRT display 32. Available for selection are the processed EMG signal which synchronizes the display to respiration; the processed EKG signal which synchronizes the display to heart rate; STIM to synchronize to the detected apnea event; XTAL to synchronize to an internal time standard; and provision for an externally applied synchronization signal.

Control 70 continuously varies the amplitude for the trigger of the synchronization signal. This adjustment may be necessary as some of the synchronization signals are extremely complex, even after processing. After proper adjustment of control 70, each of the separate traces 56, 58, 60, 62, 64, 66, and 68 are synchronized to the synchronization signal selected by multiposition control 40.

Switches 42, 44, 46, 48, 50, 52, and 54 are push buttons which turn the corresponding traces on and off. Switch 42 corresponds to the EKG signal and trace 56. Switch 44 corresponds to the pressure sensor and trace 58. Similarly, switches 46, 48, 50, 52, and 54 correspond to the differential pressure sensor, audio sensor, airflow sensor, strain gauge, and EMG sensor, respectively. These switches enable traces 60, 62, 64, 66, and 68, respectively. Trace 69 represents the stimulation signal as generated by screening device 14. This display permits visual correlation between sensed signals and stimulation signals. In this manner, trace 69 functions similar to the Medtronic ® MarkerChannel ™ cardiac pacing timing signal.

Continuous amplitude controls 72, 74, 76, 78, 80, 82, and 84 correspond to detection amplitude for EKG, pressure, differential pressure, audio, airflow, strain, and EMG sensors, respectively. These controls vary the gain of the corresponding sensor input to adjust detection level of the sensed event. Continuous threshold adjustments 86, 88, 90, 92, 94, 96, and 98 determine the event detection threshold for the corresponding sensor signal. In this manner, the operator of screening device 14 is able to determine whether detection of an obstructive apnea event is feasible with a given sensor or combination of sensors.

Indicator light 100 is illuminated upon detection of a QRS event in the EKG signal. The EKG processing channel is used primarily as a control channel. However, indicator lamps 102, 104, 106, 108, 110, and 112 are illuminated upon detection of an apnea event by sensing pressure, differential pressure, audio, airflow, muscle strain, and EMG, respectively. The operator of screening device 14 employs these indicators along with display 32 to gain confidence that an implanted device could detect apnea.

As explained above, area 30 contains the controls for the individual stimulation electrodes. The operator of screening device 14 utilizes these controls to determine the most appropriate combination of stimulation sensors and the stimulation parameters to be used therewith. These controls are arranged in columns wherein each column corresponds to a different electrode and rows wherein each row corresponds to a given type of control for each of the separate electrodes.

The first row of controls, consisting of switches 114, 116, 118, 120, 122, 124, 126, and 128, are on/off switches used to activate and deactivate the electrodes individually. These correspond to left lower, right lower, left upper, right upper, left needle, right needle, left surface, and right surface electrodes, respectively. It should be noted that the operator of screening device 14 may redefine these electrode types as necessary.

Continuous controls 130, 132, 134, 136, 138, 140, 142, and 144 are used to control the initial pulse width of the stimulation signal applied to each of the corresponding electrodes. Similarly, continuous controls 146, 148, 150, 152, 154, 156, 158, and 160 are used to adjust the final pulse width. In this way, the operator of screening device 14 can select a pulse width which varies from pulse to pulse over a given pulse train. Normally, the initial pulse will have a greater duration than the final pulse of a pulse train, however, these controls are sufficiently general that this is not required.

The interval between individual pulses in a pulse train are adjusted by continuous controls 162, 164, 166, 168, 170, 172, 174, and 176. These pulse intervals are set independently of the corresponding initial and final pulse widths. Continuous controls 178, 180, 182, 184, 186, 188, 190, and 192 vary the duty cycle of the corresponding channels. In this context, duty cycle varies as the amount of time between pulse trains of a given stimulation channel.

Just as pulse width is adjustable from initial to final pulse of a given pulse train for each stimulation channel, continuous controls 194, 196, 198, 200, 202, 204, 206, 208, 210, 212, 214, 216, 218, 220, 222, and 224 set the amplitude of the initial and final pulses of a given pulse train for each stimulation channel. Similarly, pulse amplitude varies from the initial pulse amplitude to the final pulse amplitude during each pulse train for each stimulation channel.

Switches 226, 228, 230, 232, 234, 236, 238, and 240 are double throw switches to select manual or automatic generation of stimulation signals for each of the stimulation channels. Manual generation is accomplished by switches 114, 116, 118, 120, 122, 124, 126, and 128. In the automation mode, the corresponding stimulation channel produces a stimulation pulse train upon detection of any apnea event as indicated by indicator lights 100, 102, 104, 106, 108, 110, and 112. The manual mode is ordinarily used for electrode selection and gross parameter adjustment. This corresponds to the initial preoperative screening. The automatic mode is normally used for fine adjustments and to verify automatic operation of the chosen sensor and electrode configurations. This mode is most often used during intraoperative use.

In the automatic mode, multiposition switches 242, 244, 246, 248, 250, 252, 254, and 256 select which of the sensor channels is to be used to automatically trigger a given stimulation channel. These switches are used in the selection process to determine the preferred combination of sensor and stimulation channels. Continuous controls 258, 260, 262, 264, 266, 268, 270, and 272 permit the operator of screening device 14 to select the optimum delay between detection of an apnea event and initiation of the stimulation signal.

Continuous controls 276, 278, 280, 282, 284, 286, 288, and 290 adjust the duty cycle in the coupling between the selected sensor channel and the given stimulation channel. In this context, duty cycle determines the number of sensing events necessary to trigger automatic generation of the stimulation pulse train. Certain sensors, such as pressure, may reliably indicate an apnea event upon a single sensor report. Other sensors, such as audio alert, may need several sequential detections to eliminate excess false positives.

For each stimulation channel, multiposition switch 309, 310, 312, 314, 316, 318, 320, or 322 selects one of the stimulation parameters of that stimulation channel to be displayed. The value is displayed on the corresponding one of digital displays 292, 294, 296, 298, 300, 302, 304, and 306. These displays may be used to record the parameters selected for a given stimulation channel. Printer 26 (see also FIG. 1) may also be used for that purpose.

Figure 4A:
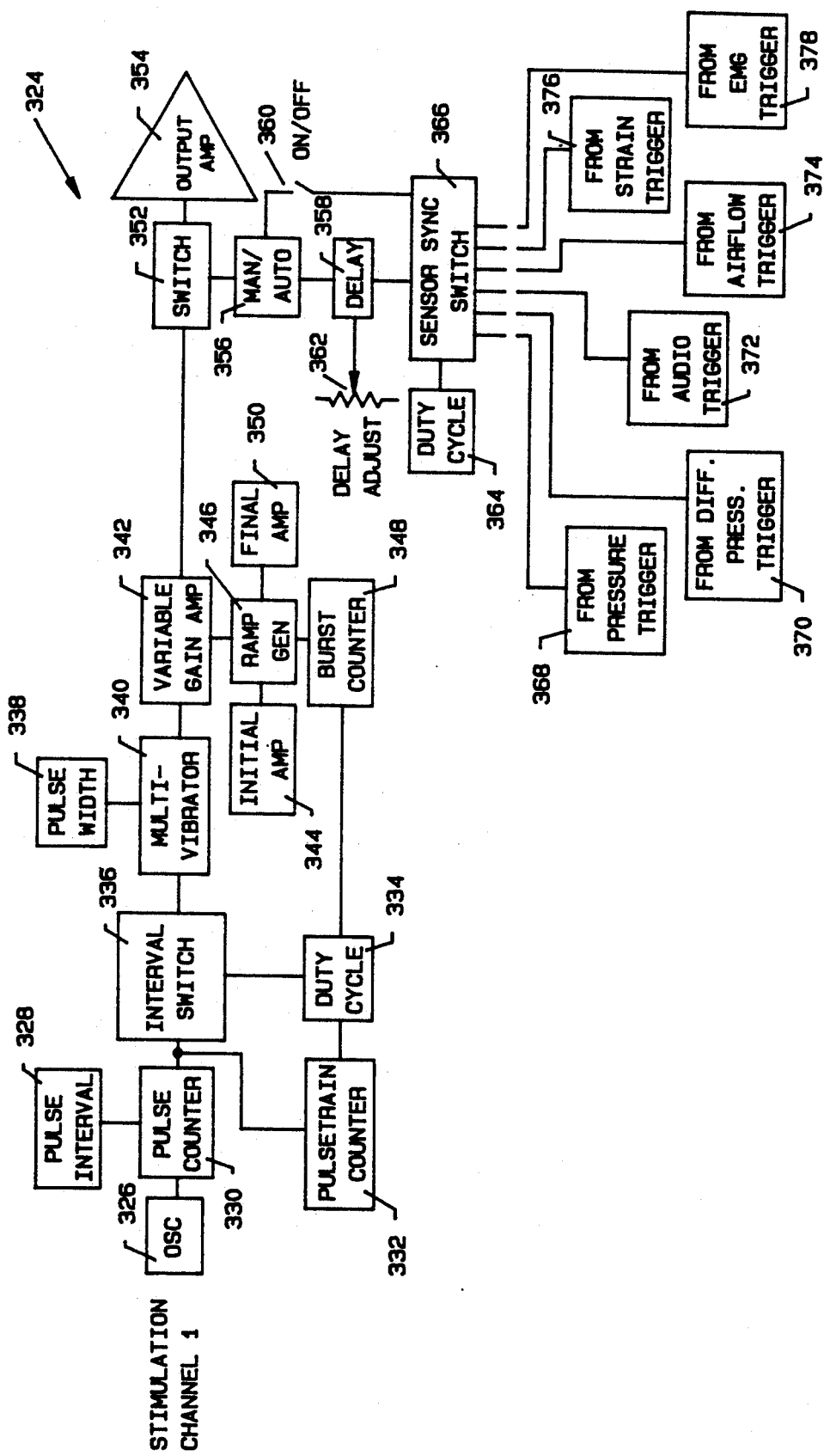
FIGS. 4A and 4B, is a block diagram of the screening device.

FIG. 4A is a block diagram 324 for one of the stimulation channels. For purposes of clarity of description, only one stimulation channel is shown. However, each of the remaining stimulation channels is similarly constructed and operates in a similar fashion.

Oscillator 326 provides the time standard for generation of the stimulation pulse train. Even though most of the elements of block diagram 324 are unique to the corresponding stimulation channel, oscillator 326 is common to all stimulation channels.

The output of oscillator 326 is counted by pulse counter 330. Pulse interval circuit 328 counts a number of outputs from oscillator 326 representative of the time between individual pulses of the pulse train. Pulse interval circuit 328 is controlled by a corresponding one of the continuous controls 162, 164, 166, 168, 170, 172, 174, and 176. Pulsetrain counter circuit 332 counts the number of pulses within a pulse train. This is not an operator adjustable parameter. However, this value may be adjusted at the time of manufacture or by maintenance personnel.

Duty cycle circuit 334 determines the time between pulse bursts within the pulse train. This value is adjusted by continuous controls 178, 180, 182, 184, 186, 188, 190, and 192. Interval switch 336 acts as a pulse burst gate to enable pulse bursts at the duty cycle as output from duty cycle circuit 334.

The individual pulses output from interval switch 336 are shaped by multivibrator 340. Each individual pulse is given a length as determined by pulse width circuit 338. The pulse width circuit 338 contains a ramp generator which proceeds from the initial pulse width selected by continuous controls 130, 132, 134, 136, 138, 140, 142, and 144 to the final pulse width selected by continuous controls 146, 148, 150, 152, 154, 156, 158, and 160. This ramp generator varies the width of each pulse in the burst.

The burst of pulses output by multivibrator 340 is supplied to variable gain amplifier 342. Gain of the individual pulses in the burst are varied by the output of ramp generator 346. The initial value of the ramp is set by continuous controls 194, 196, 198, 200, 202, 204, 206, and 208 acting through initial amplifier circuit 344. Similarly, continuous controls 210, 212, 214, 216, 218, 220, 222, and 224 acting through final amplifier circuit 350 sets the amplitude of the final pulse in the burst. Burst counter 348 resets ramp generator 346 after the completion of each complete burst.

Switch 352 serves as the final output enable for the stimulation channel. It is controlled by switches 114, 116, 118, 120, 122, 124, 126, and 128 (shown as on/off switch 360) whenever switch 356 (see switches 226, 228, 230, 232, 234, 236, 238, and 240 of FIG. 3) is in the manual position. As explained above, automatic operation provides enablement of the stimulation channel as a result of apnea event detection.

In the automatic mode, sensor synchronization switch 366 (see multiposition switches 242, 244, 246, 248, 250, 252, 254, and 256 on FIG. 3) selects one of the various sensor inputs shown as pressure trigger 368, differential pressure trigger 370, audio trigger 372, airflow trigger 374, strain trigger 376, and EMG trigger 378. Duty cycle circuit 364 adjusts the coupling in accordance with the setting of continuous controls 276, 278, 280, 282, 284, 286, 288, and 290. The synchronization signal is delayed by variable delay circuit 348 based upon the setting of the corresponding one of continuous controls 258, 260, 262, 264, 266, 268, 270, and 272 as symbolized by delay adjust 362.

Figure 4B:
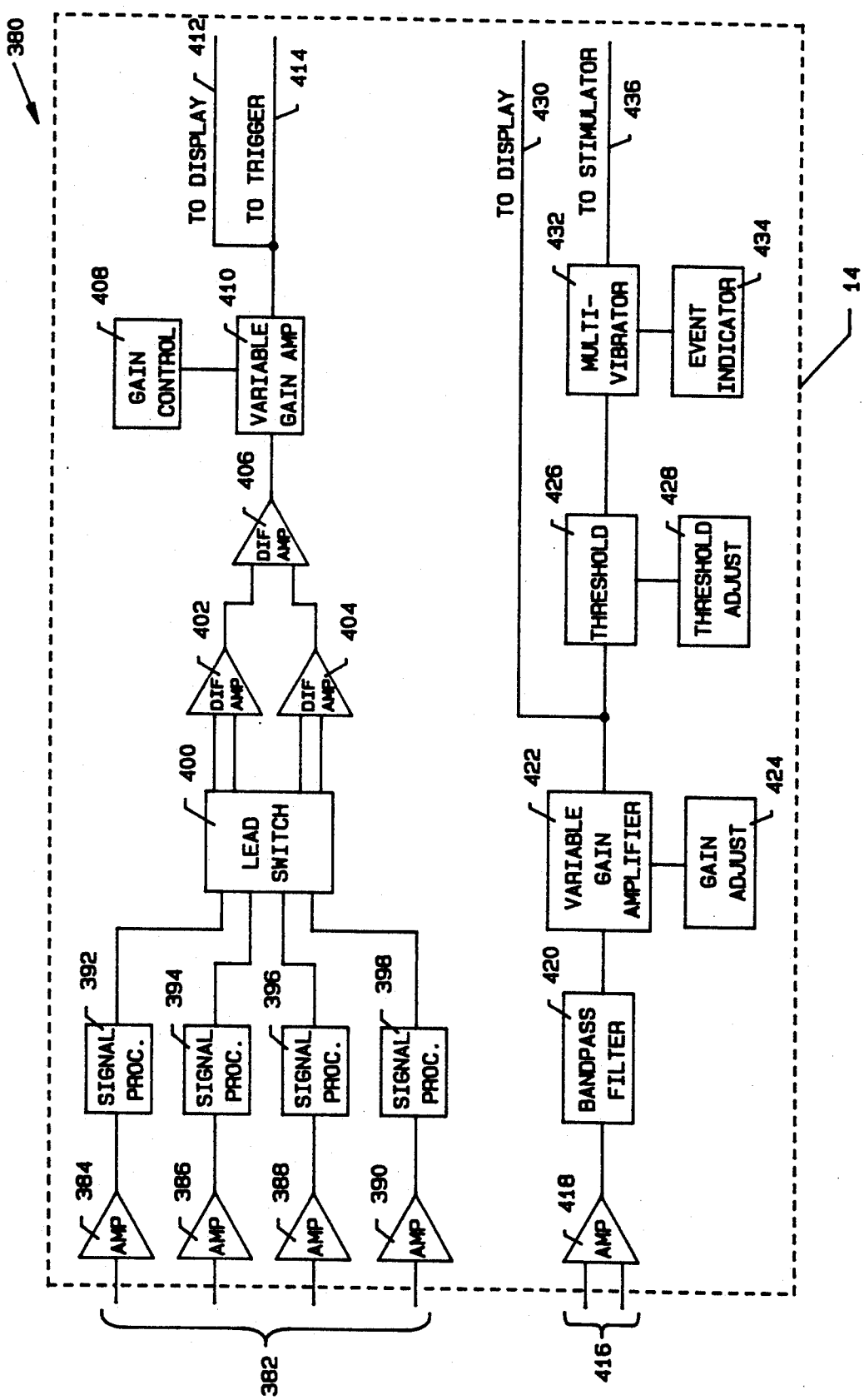

FIG. 4B is block diagram 380 of the EKG processing channel and one of the other sensor processing channels. The EKG channel is shown because it is unique. The remaining channels are similar so that only one such channel is shown for purposes of clarity.

The EKG inputs from the four limbs of patient 10 (see also FIG. 1) are shown as input 382. Each of the four individual signals is amplified by a corresponding one of the sense amplifiers 384, 386, 388, and 390. Lead switch circuit 400 selects one of the normal EKG leads known in the art. The corresponding outputs of lead switch circuit 400 are presented to differential amplifiers 402 and 404. Differential amplifier 406 determines the relationship of the outputs of differential amplifiers 402 and 404, producing a standard EKG signal at its output.

The gain of the EKG signal is varied by variable gain amplifier 410 in response to gain control circuit 408. Continuous control 72 (see also FIG. 3) determines the gain as controlled by gain control circuit 408. The processed EKG signal is supplied to synchronize display 32 via line 412 and to trigger one or more stimulation channels via line 414.

The remaining channel shown in block diagram 380 is one of the similar channels used to process each of the sensors. Because of the similarity of the channels, only one channel is shown for clarity. The sensor signal 416 is amplified by sense amplifier 418. Bandpass filter 420 selects the desired portion of the spectrum and rejects the undesired portions to improve the signal to noise ratio.

The filtered sensor signal is amplified by variable gain amplifier 422 with a gain determined by gain adjust circuit 424. This circuit is controlled by continuous control 74, 76, 78, 80, 82, or 84 (see also FIG. 3). Line 430 conveys the processed sensor signal to display 32 via switches 44, 46, 48, 50, 52, and 54 (see also FIG. 3). That same signal is presented to threshold circuit 426, which determines whether the amplitude of the sensor signal exceeds a predetermined threshold value. Exceeding that value is defined as a sensed apnea event.

The predetermined threshold value is set by continuous controls 86, 88, 90, 92, 94, 96, and 98 (see also FIG. 3). Threshold adjust circuit 428 uses this value to control the threshold of threshold circuit 426. The output of threshold circuit 426 is presented to multivibrator 432 which ensures that the signal indicating a detected apnea event has a predetermined duration. The duration of the output of multivibrator 432 is adjustable by maintenance personnel only and is not modifiable by the operator of screening device 14. Indicator lamps 100, 102, 104, 106, 108, 110, and 112 give a visual indication of the detected event by being driven by event indicator circuit 434. The output of multivibrator 432 is also coupled via lead 436 to the stimulation area for use in automatically triggering generation of a stimulation pulse train. As explained above, the remaining sensor channels are similarly constructed.

Figure 5A:
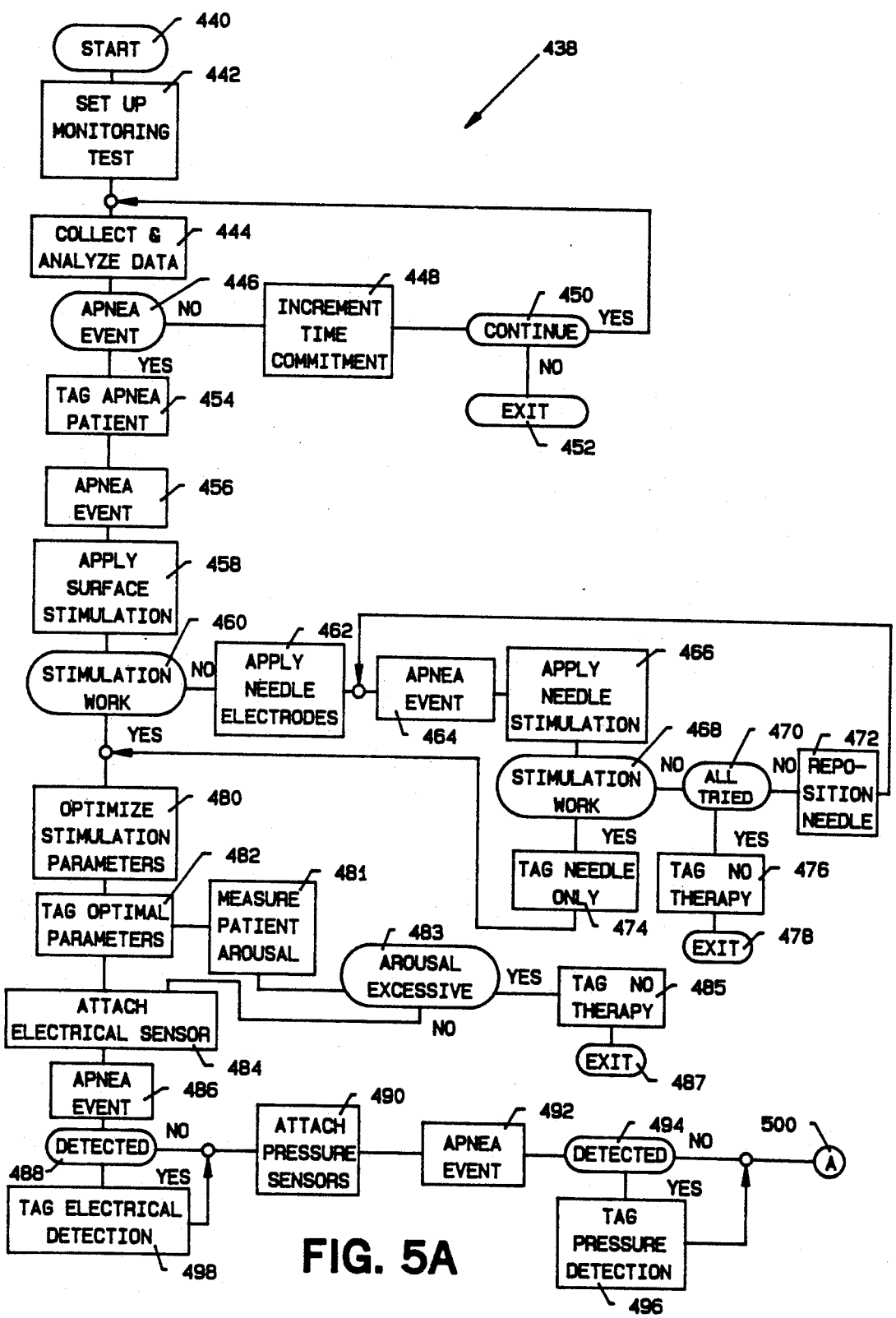
FIGS. 5A and 5B, is a flow chart of the steps used to employ the preoperative procedure.
Figure 5B:
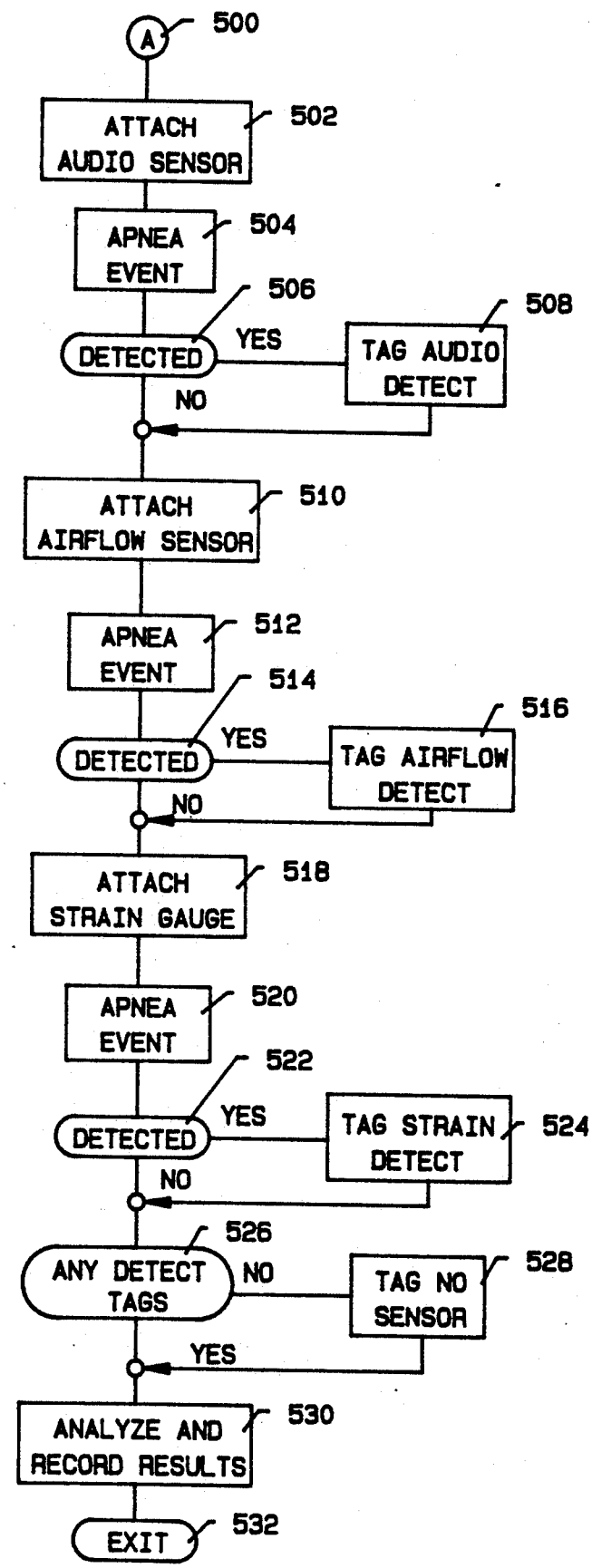

FIG. 5, comprising FIG. 5A and FIG. 5B, is a flow chart 438 for preoperative screening of patient 10. This screening is used to determine whether patient 10 is indicated for implantation of an electrical device for the treatment of obstructive sleep apnea. The procedure also provides an indication of which sensors and electrode placements are most appropriate. Gross measurement of the implant parameters is also provided.

The procedure is begun at element 440. Patient 10 is prepared for screening in the sleep laboratory at element 442 by being made comfortable on examining table or bed 12 (see also FIG. 1) and the various sensors and electrodes are properly positioned. At element 444 the various data are collected and analyzed to determine whether patient 10 experiences obstructive sleep apnea. It is often clinically useful to monitor EEG and occipital EMG according to known methods to track presence and quality of sleep in patient 10. If element 446 determines that no apnea event has been observed, the wait time is incremented at element 448. Element 450 determines if additional time is to be committed to the procedure. If not, an implanted muscle stimulation system 10 is not indicated for patient 10 and the screening procedure concludes at element 452. Note that other sleep related testing may continue within the sleep laboratory environment.

After an apnea treatment system has been indicated for patient 10, the patient is so tagged in the records at element 454. In element 456 an apnea event is precipitated. This may be by causing patient 10 to go to sleep or may occur in other ways. After the apnea event has occurred, surface stimulation is applied at element 458. Element 460 determines whether the surface stimulation is sufficient to terminate the apnea event.

When element 460 has determined that the apnea event has not been satisfactorily terminated with the surface stimulation, needle electrodes are placed at element 462. It is deemed that semiinvasive electrodes may be suitable to terminate the apnea event even if surface electrodes are inadequate for that task. After the needle electrodes are placed, element 464 (like element 456) again precipitates an apnea event. Electrical stimulation is applied to the needle electrodes at element 466. If element 468 determines that the needle electrode stimulation was able to terminate the apnea event, element 474 tags patient 10 as terminable using semiinvasive electrodes only.

Element 470 determines whether every reasonable placement of the needle electrodes has been tried. If yes, element 476 tags patient 10 as unsuitable for implant therapy, because of failure to terminate an apnea event using semiinvasive electrical stimulation. If element 470 finds that not all needle electrode placement positions have been tried, the needle electrodes are moved to the next position at element 472 and control is returned to element 464 to retry with the new electrode placement.

Patient 10, having had at least one apnea event terminated using either surface or needle electrodes, has the stimulation parameters optimized at element 480. These parameters are initial and final pulse width, initial and final amplitude, pulse interval, and duty cycle (see also FIG. 3 and the discussions above). The optimal stimulation parameters are recorded at element 482.

Element 481 measures the degree of patient arousal during stimulation. In some patients, there is no noticeable arousal, which is the ideal condition. However, other patients may experience unacceptable levels of arousal. If this occur as determined by element 483, implantable stimulation therapy is contraindicated as not sufficiently efficacious. Element 485 tags the patient as not a candidate and exit is obtained at element 487. This completes the preoperative screening for effectiveness and optimization of electrical stimulation.

The selection, placement, and parameter optimization regarding the sensors is initiated at element 484 with placement of the EMG sensing electrodes. An apnea event is precipitated at element 486. Element 488 determines whether the EMG sensors have detected the event. If yes, element 498 records that an event can be detected using EMG sensing. Element 490 sets up the pressure sensors. An apnea event is precipitated at element 492. It is determined at element 494 whether the apnea event can be detected using pressure or differential pressure measurement. If yes, element 496 records that an apnea event is detectable using pressure and/or differential pressure sensing. Control passes to the flow chart of FIG. 5B via element 500.

The audio sensor is positioned at element 502. An apnea event occurs again at element 504. Detection is attempted at element 506. If the audio sensor properly detected the apnea event, element 508 records the suitability of an audio sensor. The airflow sensor is positioned and attached at element 510. An apnea event is simulated at element 512. Detection of the simulated apnea event using the airflow sensor is attempted at element 514. If detection is accomplished, element 516 records the success. The strain gauge is positioned at element 518. Element 520 results in precipitation of an apnea event. Detection using the strain gauge is attempted at element 522. If detection is accomplished, element 524 records detection using the strain gauge.

Having thus attempted detection using all of the available sensors, element 526 determines if any successful detections were made. If no, automatic therapy using an implanted system is contraindicated for patient 10 and this finding is recorded at element 528. The screening results are analyzed and recorded at element 530. This may include printing on printer 26 (see also FIG. 1), for example. The preoperative screening procedure is completed at element 532.

Figure 6:
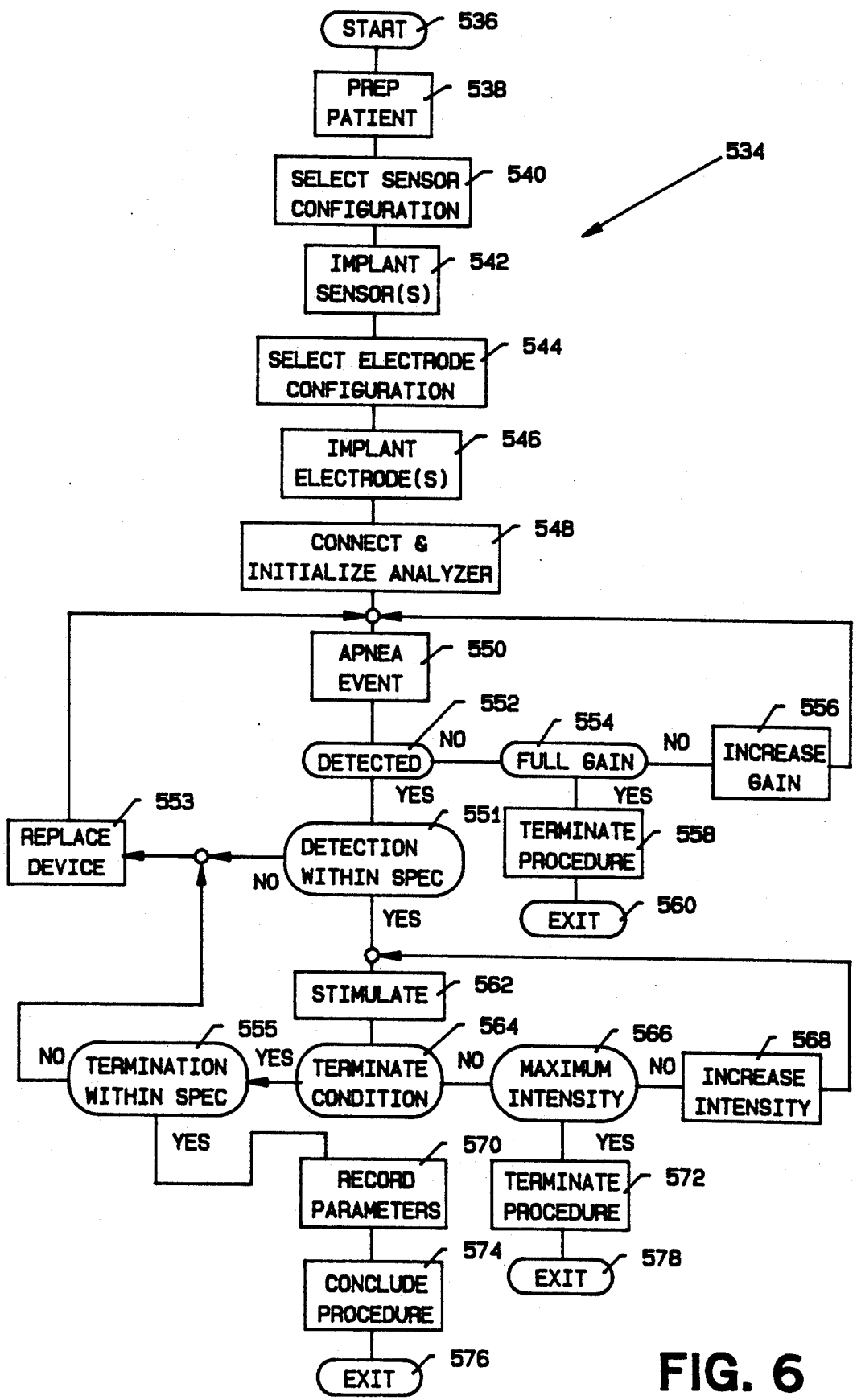
FIG. 6 is a flow chart showing the steps used to employ the intraoperative procedure.

FIG. 6 is a flow chart 534 for an intraoperative screening procedure. The procedure is begun at element 536. Patient 10 is prepped for surgery at element 538. The sensor configuration is selected at element 540. This selection is based upon the preoperative screening discussed above. The sensor(s) is implanted at element 542. Similarly, the electrode configuration is selected at element 546, and the electrodes are implanted at element 546. Element 548 involves coupling of the newly implanted sensor(s) and electrode(s) to screening device 14. An apnea event occurs at element 550. Detection of the apnea event is attempted at element 552. If the event is not detected, the sensor gain is checked at element 554. Element 556 continues to increase the gain and reattempt detection until either detection is accomplished or the maximum sensor gain has been reached. Element 558 terminates the procedure if detection is not accomplished and exit is obtained at element 560.

Assuming that successful detection has been accomplished using the selected sensor configuration, element 551 determines whether the sensor performance of the implantable device is within the specifications of the manufacturer. If not, the implantable device is replaced at element 553. After the implantable device has been determined to be operating within specifications, element 562 initiates stimulation using the implanted electrodes. Element 564 determines if the apnea event is terminated or prevented. If not, element 566 determines whether the maximum stimulation intensity has been reached. If yes, the procedure is terminated at element 572. If not, element 568 increases the stimulation intensity and attempts termination again.

After successful termination of the apnea event, element 555 determines whether the stimulation function of the implantable device has performed within the manufacturer's specifications. If not, the implantable device is replaced at element 553 and the testing procedure is repeated. After it is determined that the implantable device is operating properly, the stimulation parameters are recorded at element 570. The surgical procedure is concluded at element 574. Exit is accomplished at element 576.

Having thus described the preferred embodiments of the present invention, those of skill in the art will be readily able to apply the teachings found herein to yet other embodiments within the scope of the claims hereto attached.

We claim:

1. An apparatus for screening obstructive sleep apnea patients comprising:
   a. a housing;
   b. means located within said housing for processing signals from a plurality of sensors adapted to monitor a plurality of different physiological parameters;
   c. means located within said housing and coupled to said processing means for determining detection of an apnea event from a one of said plurality of sensors;
   d. means located within said housing for generating a muscle stimulating signal; and
   e. means located within said housing and coupled to said determining means and said generating means for causing said generating means to be initiated by determination of detection of said apnea event.

2. An apparatus according to claim 1 wherein said processing means further comprises a variable gain amplifier for each of said plurality of sensors.

3. An apparatus according to claim 2 wherein said processing means further comprises a variable threshold adjustment for each of said plurality of sensors.

4. An apparatus according to claim 3 wherein said processing means further comprises a visual event indicator for each of said plurality of sensors.

5. An apparatus according to claim 4 wherein said processing means further comprises a CRT display for displaying each of said plurality of sensors.

6. An apparatus according to claim 1, 2, 3, 4, and 5 wherein said generating means further comprises a plurality of individually controlled output channels.

7. An apparatus according to claim 6 wherein each of said plurality of separately controlled output channels further comprises means for adjusting initial and final pulse width.

8. An apparatus according to claim 7 wherein each of said plurality of separately controlled output channels further comprises means for controlling pulse interval.

9. An apparatus according to claim 8 wherein each of said plurality of separately controlled output channels further comprises means for controlling duty cycle.

10. An apparatus according to claim 9 wherein each of said plurality of separately controlled output channels further comprises means for adjusting initial and final amplitude.

11. A method of screening apnea patients comprising:
   a. simultaneously measuring a plurality of sensors for detection of an apnea event;
   b. testing a plurality of electrodes for termination of an apnea event;
   c. optimizing parameters associated with processing of signals from said plurality of sensors; and
   d. optimizing parameters associated with stimulation at said plurality of electrodes for termination of said apnea event.

* * * * *